(12) United States Patent
Yoneda et al.

(10) Patent No.: US 11,999,681 B2
(45) Date of Patent: *Jun. 4, 2024

(54) ALKYL SULFATE ESTER OR SALT OF SAME

(71) Applicant: DAIKIN INDUSTRIES, LTD., Osaka (JP)

(72) Inventors: Satoru Yoneda, Osaka (JP); Masahiro Higashi, Osaka (JP); Akiyoshi Yamauchi, Osaka (JP); Sumi Ishihara, Osaka (JP); Yosuke Kishikawa, Osaka (JP); Marina Nakano, Osaka (JP); Shinnosuke Nitta, Osaka (JP); Hirokazu Aoyama, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/498,576

(22) PCT Filed: Mar. 30, 2018

(86) PCT No.: PCT/JP2018/013625
§ 371 (c)(1),
(2) Date: Sep. 27, 2019

(87) PCT Pub. No.: WO2018/181906
PCT Pub. Date: Oct. 4, 2018

(65) Prior Publication Data
US 2020/0399211 A1 Dec. 24, 2020

(30) Foreign Application Priority Data
Mar. 31, 2017 (JP) .................. 2017-073085

(51) Int. Cl.
*C07C 305/10* (2006.01)
*C07C 303/24* (2006.01)

(52) U.S. Cl.
CPC .......... *C07C 305/10* (2013.01); *C07C 303/24* (2013.01)

(58) Field of Classification Search
None
See application file for complete search history.

(56) References Cited

U.S. PATENT DOCUMENTS

| | | | |
|---|---|---|---|
| 3,793,210 A | 2/1974 | Corey | |
| 11,518,826 B2 * | 12/2022 | Mishima | C08F 2/26 |
| 2004/0053158 A1 | 3/2004 | Yamato et al. | |
| 2008/0093582 A1 | 4/2008 | Nagai et al. | |
| 2009/0181952 A1 | 7/2009 | Haydar et al. | |
| 2012/0116003 A1 | 5/2012 | Brothers et al. | |
| 2012/0283382 A1 | 11/2012 | Spada et al. | |
| 2016/0108225 A1 | 4/2016 | Toyoda et al. | |
| 2020/0172476 A1 | 6/2020 | Yoneda et al. | |
| 2020/0255551 A1 * | 8/2020 | Taira | C08F 6/16 |
| 2020/0399211 A1 | 12/2020 | Yoneda et al. | |
| 2021/0115224 A1 * | 4/2021 | Kato | C08K 5/098 |
| 2022/0169830 A1 * | 6/2022 | Kato | C08K 5/098 |

FOREIGN PATENT DOCUMENTS

| | | |
|---|---|---|
| CN | 102382323 A | 3/2012 |
| CN | 105367692 A | 3/2016 |
| CN | 109715603 A | 5/2019 |
| EP | 1 894 970 A1 | 3/2008 |
| EP | 2 703 557 A1 | 3/2014 |
| EP | 3 514 138 A1 | 7/2019 |
| EP | 3 514 142 A1 | 7/2019 |
| GB | 2517481 A | 2/2015 |
| JP | 40-21438 B | 9/1965 |
| JP | 49-029294 A | 3/1974 |
| JP | 07-264461 A | 10/1995 |
| JP | 9-503295 A | 3/1997 |
| JP | 10-338617 A | 12/1998 |
| JP | 11-029788 A | 2/1999 |
| JP | 11-507956 A | 7/1999 |
| JP | 2000-001467 A | 1/2000 |
| JP | 2004-526984 A | 9/2004 |
| JP | 2005-325327 A | 11/2005 |
| JP | 2006-008517 A | 1/2006 |
| JP | 2010-511096 A | 4/2010 |
| JP | 6888669 B2 | 6/2021 |
| WO | 95/08529 A1 | 3/1995 |
| WO | 97/39088 A1 | 10/1997 |
| WO | 2008/066839 A1 | 6/2008 |
| WO | 2012/116238 A1 | 8/2012 |
| WO | 2013/016372 A1 | 1/2013 |
| WO | WO2018181898 * | 10/2018 |
| WO | WO2019031617 * | 2/2019 |

(Continued)

OTHER PUBLICATIONS

Federal Register, vol. 72, No. 161, Aug. 21, 2007, p. 46722.*
Grant & Hackh's Chemical Dictionary (5th Ed. 1987) at p. 148.*
Chemical Abstract Registry No. 1823379-33-4, indexed in the Registry File on STN CAS Online Dec. 6, 2015.*
Machine-generated English translation of Foreign Patent Application No. WO2019031617, published on Feb. 14, 2019.*
Machine-generated English translation of Foreign Patent Application No. WO2018181898, published on Oct. 4, 2018.*
Gregory R. Schulz, et al., "Micelles formed from photochemically active amphiphiles: structural characterization by small-angle neutron scattering", Journal of Molecular Structure, 1996, pp. 191-196, vol. 383.

(Continued)

*Primary Examiner* — Po-Chih Chen
(74) *Attorney, Agent, or Firm* — Sughrue Mion, PLLC

(57) ABSTRACT

An alkyl sulfate ester containing a carbonyl group or a salt thereof. The compound is represented by the following formula:

$$R^1-C(=O)-(CR^2{}_2)_n-(OR^3)_p-(CR^4{}_2)_q-L-OSO_3X$$

wherein $R^1$, $R^2$, $R^3$, $R^4$, L, X, n, p and q are as defined herein. Also disclosed is a production method for making the alkyl sulfate ester.

8 Claims, No Drawings

(56) References Cited

FOREIGN PATENT DOCUMENTS

WO    WO2019131633    *  7/2019

OTHER PUBLICATIONS

W. E. Parish, et al., "An Apparatus to Simulate Metabolism of Ingested Substances", Toxicology In Vitro, 1990, pp. 532-536, vol. 4, No. 4/5.
International Search Report for PCT/JP2018/013625 dated Jun. 12, 2018. [PCT/ISA/210].
Extended European Search Report issued Dec. 16, 2020 in European Application No. 18777204.1.
Database Caplus [Online] Chemical Abstracts Service, Columbus, Ohio, US; 1982, XP002801209, retrieved from STN Database accession No. 1982:36971 (1 page).
Database Caplus [Online] Chemical Abstracts Service, Columbus, Ohio, US; 1981, XP002801208, retrieved from STN Database accession No. 1981:499698 (2 pages total).
Estillore et al., "Water Uptake and Hygroscopic Growth of Organosulfate Aerosol", Environmental Science & Technology, Mar. 26, 2016, vol. 50, No. 8, pp. 4259-4268 (10 pages total).
Rosen et al., "Effect of Hard River Water on the Surface Properties of Surfactants", J. Chem. Eng. Data, Sep. 12, 1996, vol. 41, No. 5, pp. 1160-1167 (8 pages total).
Someya et al., "Silver-catalyzed cross-coupling reactions of alkyl bromides with alkyl or aryl Grignard reagents", Tetrahedron Letters, Feb. 10, 2009, vol. 50, No. 26, pp. 3270-3272 & pp. S1-S52 (55 pages total).
International Preliminary Report on Patentability with a Translation of Written Opinion in International Application No. PCT/JP2018/013625, dated on Oct. 1, 2019.
International Search Report for related PCT/JP2018/013605, dated Jun. 26, 2018.
International Preliminary Report on Patentability and Translation of Written Opinion from the International Bureau in related International Application No. PCT/JP2018/013605, dated Oct. 1, 2019.
Communication dated Dec. 14, 2020, issued by the European Patent Office in application No. 18776956.7.
Restriction Requirement issued Mar. 4, 2021 in related U.S. Appl. No. 16/498,849.
Restriction Requirement issued Mar. 15, 2021 in related U.S. Appl. No. 16/498,849.
Yasa Sathyam Reddy et al., "Synthesis and Evaluation of Surface and Biological Properties of Some Lactic Acid-Based Anionic Surfactants", J Surfact Deterg, 2016, vol. 19, pp. 343-351 (9 pages).
Hettiyadura et al., "Qualitative and quantitative analysis of atmospheric organosulfates in Centreville, Alabama", Atomospheric Chemistry and Physics, 2017, 17, pp. 1343-1359 (17 page total).
Extended European Search Report dated Jun. 22, 2021 from the European Patent Office in related EP Application No. 21159543.4.
Communication dated May 11, 2021, from the European patent Office in application No. 18776956.7.
Database CA [Online] Chemical Abstracts Service, Columbus, Ohio, US; Votapek, Vaclav et al, "Low-foam surfactants with high activity and resistance to hot alkalies", XP002802821, (1 page total); Jun. 29, 1979.
Deepak B. Salunke et al. "Design and Development of Stable, Water-Soluble, Human Toll-like Receptor 2 Specific Monoacyl Lipopeptides as Candidate Vaccine Adjuvants", Journal of Medicinal Chemistry, vol. 56, No. 14, 2013, pp. A-P (16 pages total).
Xin Fan et al. "Oxygenated Hydrocarbon Ionic Surfactants Exhibit $CO_2$ Solubility" Journal of the American Chemical Society, vol. 127, No. 33, 2005, pp. 11754-11762 (9 pages total).
Hermann Schlenk et al., "Syntheses of Derivatives of Dihydroxyacetone and of Glycerides" Journal of the American Society, vol. 74, No. 10, 1952, pp. 2550-2552 (3 pages total).
Communication dated Jun. 9, 2021, from the United States Patent and Trademark Office in U.S. Appl. No. 16/498,849.
Notice of Allowance dated Nov. 16, 2021, from the United States Patent and Trademark Office in U.S. Appl. No. 16/498,849.
Zarzar et al., "Dynamically reconfigurable complex emulsions via tunable interfacial tensions", Nature, 2015, vol. 518, No. 7540, pp. 520-524 (5 pages total).
Forbes et al., "Unusual Dynamics of Micellized Radical Pairs Generated from Photochemically Active Amphiphiles", J. Am. Chem. Soc., 1996, vol. 118, No. 43, pp. 10652-10653 (2 pages total).
Registry(STN)[online], 1984-2004, [Search date: Dec. 20, 2021] CAS Registry No. 78568-77-1, 763024-63-1, 790188-03-3 (3 pages total).

* cited by examiner

ALKYL SULFATE ESTER OR SALT OF SAME

CROSS REFERENCE TO RELATED APPLICATIONS

This application is a National Stage of International Application No. PCT/JP2018/013625, filed on Mar. 30, 2018, which claims priority from Japanese Patent Application No. 2017-073085, filed on Mar. 31, 2017.

TECHNICAL FIELD

The invention relates to alkyl sulfate esters or salts thereof.

BACKGROUND ART

Non-Patent Literature 1 discloses, as an intermediate metabolite of sodium lauryl sulfate, a compound that is presumed to be 11-keto dodecyl sulphate.

CITATION LIST

Non-Patent Literature

Non-Patent Literature 1: W. E. Parish, and three others, "AN APPARATUS TO SIMULATE METABOLISM OF INGESTED SUBSTANCES", Toxicology in Vitro, 1990, Vol. 4, No. 4/5, pp. 532-536

SUMMARY OF INVENTION

Technical Problem

The invention aims to provide a novel alkyl sulfate ester containing a carbonyl group or a salt thereof.

Solution to Problem

The invention relates to a compound represented by the following formula:

[Chem. 1]

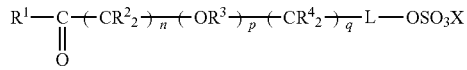

wherein $R^1$ is a linear or branched alkyl group containing one or more carbon atoms and optionally containing a substituent or a cyclic alkyl group containing three or more carbon atoms and optionally containing a substituent, and optionally contains a monovalent or divalent heterocycle or optionally forms a ring when containing three or more carbon atoms;

$R^2$ and $R^4$ are each individually H or a substituent;

$R^3$ is a C1-C10 alkylene group optionally containing a substituent;

n is an integer of 1 or greater;

p and q are each individually an integer of 0 or greater;

X is H, a metal atom, $NR^5_4$, imidazolium optionally containing a substituent, pyridinium optionally containing a substituent, or phosphonium optionally containing a substituent, where $R^5$s are each H or an organic group and are the same as or different from each other;

any two of $R^1$, $R^2$, $R^3$, and $R^4$ optionally bind to each other to form a ring; and L is a single bond, —CO$_2$—B—*, —OCO—B—*, —CONR$^6$—B—*, —NR$^6$CO—B—*, or —CO— other than the carbonyl groups in —CO$_2$—B—, —OCO—B—, —CONR$^6$—B—, and —NR$^6$CO—B—, where B is a single bond or a C1-C10 alkylene group optionally containing a substituent, $R^6$ is H or a C1-C4 alkyl group optionally containing a substituent, and * indicates the bond to —OSO$_3$X in the formula.

The compound preferably contains 3 to 30 carbon atoms in total.

L is preferably a single bond.

$R^2$ and $R^4$ are each preferably H or a C1-C4 linear or branched alkyl group.

$R^3$ is preferably a C1-C4 alkylene group free from a substituent.

$R^1$ is a C1-C4 linear or branched alkyl group.

The compound preferably excludes 11-keto dodecyl sulphate.

X in the formula is preferably a metal atom or $NR^5_4$, wherein $R^5$ is defined as described above.

The compound is preferably an aqueous dispersant.

The invention also relates to a production method including:

a step (41) of oxidizing a compound (10) represented by the following formula:

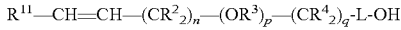

wherein $R^2$ to $R^4$, n, p, and q are defined as described above;

$R^{11}$ is H, a linear or branched alkyl group containing one or more carbon atoms and optionally containing a substituent, or a cyclic alkyl group containing three or more carbon atoms and optionally containing a substituent, and optionally contains a monovalent or divalent heterocycle or optionally forms a ring when containing three or more carbon atoms; and L is a single bond, —CO$_2$—B—*, —OCO—B—*, —CONR$^6$—B—*, —NR$^6$CO—B—*, or —CO— other than the carbonyl groups in —CO$_2$—B—, —OCO—B—, —CONR$^6$—B—, and —NR$^6$CO—B—, where B is a single bond or a C1-C10 alkylene group optionally containing a substituent, $R^6$ is H or a C1-C4 alkyl group optionally containing a substituent, and * indicates the bond to —OH in the formula, to provide a compound (41) represented by the following formula:

[Chem. 2]

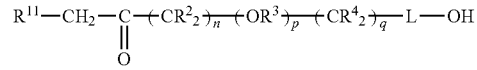

wherein $R^2$ to $R^4$, $R^{11}$, L, n, p, and q are defined as described above; and a step (42) of sulfuric-esterifying the compound (41) to provide a compound (42) represented by the following formula:

[Chem. 3]

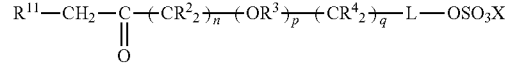

wherein $R^2$ to $R^4$, $R^{11}$, L, n, p, q, and X are defined as described above.

L is preferably a single bond.

Advantageous Effects of Invention

The compound of the invention is a compound exhibiting a surfactant activity, and can suitably be used as an aqueous dispersant.

The production method of the invention can suitably produce the compound of the invention.

DESCRIPTION OF EMBODIMENTS

The invention is described in detail below.

The term "organic group" as used herein means a group containing one or more carbon atoms or a group obtainable by removing one hydrogen atom from an organic compound, unless otherwise mentioned.

Examples of the "organic group" include:
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents,
a heteroaryl group optionally containing one or more substituents,
a cyano group,
a formyl group,
RaO—,
RaCO—,
RaSO$_2$—,
RaCOO—,
RaNRaCO—,
RaCONRa—,
RaOCO—, and
RaOSO$_2$—,
wherein each Ra is independently
an alkyl group optionally containing one or more substituents,
an alkenyl group optionally containing one or more substituents,
an alkynyl group optionally containing one or more substituents,
a cycloalkyl group optionally containing one or more substituents,
a cycloalkenyl group optionally containing one or more substituents,
a cycloalkadienyl group optionally containing one or more substituents,
an aryl group optionally containing one or more substituents,
an aralkyl group optionally containing one or more substituents,
a non-aromatic heterocyclic group optionally containing one or more substituents, or
a heteroaryl group optionally containing one or more substituents.

The organic group is preferably an alkyl group optionally containing one or more substituents.

The term "substituent" as used herein means a group which can replace another atom or group, unless otherwise mentioned. Examples of the "substituent" include an aliphatic group, an aromatic group, a heterocyclic group, an acyl group, an acyloxy group, an acylamino group, an aliphatic oxy group, an aromatic oxy group, a heterocyclic oxy group, an aliphatic oxycarbonyl group, an aromatic oxycarbonyl group, a heterocyclic oxycarbonyl group, a carbamoyl group, an aliphatic sulfonyl group, an aromatic sulfonyl group, a heterocyclic sulfonyl group, an aliphatic sulfonyloxy group, an aromatic sulfonyloxy group, a heterocyclic sulfonyloxy group, a sulfamoyl group, an aliphatic sulfonamide group, an aromatic sulfonamide group, a heterocyclic sulfonamide group, an amino group, an aliphatic amino group, an aromatic amino group, a heterocyclic amino group, an aliphatic oxycarbonylamino group, an aromatic oxycarbonylamino group, a heterocyclic oxycarbonylamino group, an aliphatic sulfinyl group, an aromatic sulfinyl group, an aliphatic thio group, an aromatic thio group, a hydroxy group, a cyano group, a sulfo group, a carboxy group, an aliphatic oxyamino group, an aromatic oxyamino group, a carbamoylamino group, a sulfamoyl amino group, a halogen atom, a sulfamoyl carbamoyl group, a carbamoyl sulfamoyl group, a dialiphatic oxyphosphinyl group, and a diaromatic oxyphosphinyl group.

The invention relates to a compound represented by the following formula.

[Chem. 4]

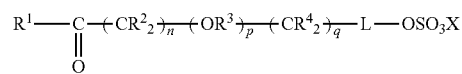

In the formula, $R^1$ is a linear or branched alkyl group containing one or more carbon atoms and optionally containing a substituent or a cyclic alkyl group containing three or more carbon atoms and optionally containing a substituent. $R^1$ is preferably a C1-C4 linear or branched alkyl group.

When containing three or more carbon atoms, the alkyl group may optionally contain a monovalent or divalent heterocycle, or may optionally form a cycle. The heterocycle is preferably an unsaturated heterocycle, more preferably an oxygen-containing unsaturated heterocycle, and may be a furan ring, for example. In $R^1$, a divalent heterocycle may be present between two carbon atoms, or a divalent heterocycle may be present at an end and bind to —C(=O)—, or a monovalent heterocycle may be present at an end of the alkyl group.

The "number of carbon atoms" in the alkyl group herein includes the number of carbon atoms constituting the heterocycles.

The compound preferably contains 3 to 30, more preferably 5 to 25, still more preferably 7 to 20 carbon atoms in total.

The substituent which may be contained in the alkyl group for $R^1$ is preferably a halogen atom, a C1-C10 linear or branched alkyl group, a C3-C10 cyclic alkyl group, or a hydroxy group, particularly preferably a methyl group or an ethyl group.

The alkyl group for $R^1$ is preferably free from a carbonyl group.

In the alkyl group, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

$R^1$ is preferably a C1-C10 linear or branched alkyl group optionally containing a substituent or a C3-C10 cyclic alkyl group optionally containing a substituent, more preferably a C1-C10 linear or branched alkyl group free from a carbonyl group or a C3-C10 cyclic alkyl group free from a carbonyl group, still more preferably a C1-C10 linear or branched alkyl group free from a substituent, further more preferably a C1-C3 linear or branched alkyl group free from a substituent, particularly preferably a methyl group (—$CH_3$) or an ethyl group (—$C_2H_5$), most preferably a methyl group (—$CH_3$).

In the formula, $R^2$ and $R^4$ are each individually H or a substituent; multiple $R^2$s may be the same as or different from each other and multiple $R^4$s may be the same as or different from each other.

The substituent for each of $R^2$ and $R^4$ is preferably a halogen atom, a C1-C10 linear or branched alkyl group, a C3-C10 cyclic alkyl group, or a hydroxy group, particularly preferably a methyl group or an ethyl group.

The alkyl group for each of $R^2$ and $R^4$ is preferably free from a carbonyl group.

In the alkyl group, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

The alkyl group for each of $R^2$ and $R^4$ is preferably a C1-C10 linear or branched alkyl group free from a carbonyl group or a C3-C10 cyclic alkyl group free from a carbonyl group, more preferably a C1-C10 linear or branched alkyl group free from a carbonyl group, still more preferably a C1-C3 linear or branched alkyl group free from a substituent, particularly preferably a methyl group (—$CH_3$) or an ethyl group (—$C_2H_5$).

$R^2$ and $R^4$ are preferably each individually H or a C1-C10 linear or branched alkyl group free from a carbonyl group, more preferably H or a C1-C4 linear or branched alkyl group, still more preferably H or a C1-C3 linear or branched alkyl group free from a substituent, particularly preferably H, a methyl group (—$CH_3$), or an ethyl group (—$C_2H_5$), most preferably H.

In the formula, $R^3$ is a C1-C10 alkylene group optionally containing a substituent. $R^3$ is preferably a C1-C4 alkylene group free from a substituent. When multiple $R^3$s are present, they may be the same as or different from each other.

The alkylene group is preferably free from a carbonyl group.

In the alkylene group, 75% or less of the hydrogen atoms binding to any of the carbon atoms may be replaced by halogen atoms, 50% or less thereof may be replaced by halogen atoms, or 25% or less thereof may be replaced by halogen atoms. The alkylene group is preferably a non-halogenated alkyl group containing no halogen atoms such as fluorine atoms and chlorine atoms.

The alkylene group preferably contains no substituent.

The alkylene group is preferably a C1-C10 linear or branched alkylene group optionally containing a substituent or a C3-C10 cyclic alkylene group optionally containing a substituent, preferably a C1-C10 linear or branched alkylene group free from a carbonyl group or a C3-C10 cyclic alkylene group free from a carbonyl group, more preferably a C1-C10 linear or branched alkylene group free from a substituent, still more preferably a methylene group (—$CH_2$—), an ethylene group (—$C_2H_4$—), an isopropylene group (—$CH(CH_3)CH_2$—), or a propylene group (—$C_3H_6$—).

Any two of $R^1$, $R^2$, $R^3$, and $R^4$ may bind to each other to form a ring, but they preferably do not form a ring.

In the formula, n is an integer of 1 or greater; n is preferably an integer of 1 to 40, more preferably an integer of 1 to 30, still more preferably an integer of 5 to 25, particularly preferably an integer of 5 to 9 and 11 to 25.

In the formula, p and q are each individually an integer of 0 or greater; p is preferably an integer of 0 to 10, more preferably 0 or 1, while q is preferably an integer of 0 to 10, more preferably an integer of 0 to 5.

The sum of n, p, and q is preferably an integer of 5 or greater. The sum of n, p, and q is more preferably an integer of 8 or greater. The sum of n, p, and q is also preferably an integer of 60 or smaller, more preferably an integer of 50 or smaller, still more preferably an integer of 40 or smaller.

In the formula, X is H, a metal atom, $NR^5_4$, imidazolium optionally containing a substituent, pyridinium optionally containing a substituent, or phosphonium optionally containing a substituent, wherein $R^5$ is H or an organic group, and the four $R^5$s are the same as or different from each other. $R^5$ is preferably H or a C1-C10 organic group, more preferably H or a C1-C4 organic group. Examples of the metal atom include alkali metals (Group 1) and alkaline earth metals (Group 2), and preferred is Na, K, or Li.

X is preferably H, a metal atom, or $NR^5_4$, more preferably H, an alkali metal (Group 1), an alkaline earth metal (Group 2), or $NR^5_4$, still more preferably H, Na, K, Li, or $NH_4$, further more preferably Na, K, or $NH_4$, particularly preferably Na or $NH_4$, most preferably $NH_4$.

In the formula, L is a single bond, —$CO_2$—B—*, —OCO—B—*, —$CONR^6$—B—*, —$NR^6CO$—B—*, or —CO— other than the carbonyl groups in —$CO_2$—B—, —OCO—B—, —$CONR^6$—B—, and —$NR^6CO$—B—, where B is a single bond or a C1-C10 alkylene group optionally containing a substituent, $R^6$ is H or a C1-C4 alkyl group optionally containing a substituent. The alkylene group more preferably contains 1 to 5 carbon atoms. $R^6$ is more preferably H or a methyl group. The symbol * indicates the bond to —$OSO_3X$ in the formula.

L is preferably a single bond.

The compound is preferably a compound represented by the following formula:

[Chem. 5]

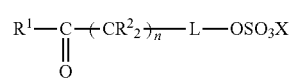

wherein $R^1$, $R^2$, L, n, and X are defined as described above.

The compound is preferably not 11-keto dodecyl sulphate. Examples of the compound include $CH_3C(O)CH_2CH_2CH_2CH_2CH_2CH_2CH_2CH_2OSO_3Na$,
$CH_3C(O)CH_2CH_2CH_2CH_2CH_2CH_2CH_2CH_2OSO_3Na$,
$CH_3C(O)CH_2CH_2CH_2CH_2CH_2CH_2CH_2OSO_3Na$,
$CH_3C(O)CH_2CH_2CH_2CH_2CH_2CH_2OSO_3Na$,
$CH_3C(O)CH_2CH_2CH_2CH_2CH_2OSO_3Na$,
$CH_3C(O)CH_2CH_2CH_2CH_2OSO_3Na$,
$(CH_3)_3CC(O)CH_2CH_2CH_2CH_2CH_2CH_2CH_2CH_2CH_2OSO_3Na$,
$(CH_3)_2CHC(O)CH_2CH_2CH_2CH_2CH_2CH_2CH_2CH_2CH_2OSO_3Na$,
$(CH_2)_5CHC(O)CH_2CH_2CH_2CH_2CH_2CH_2CH_2CH_2CH_2OSO_3Na$,
$CH_3CH_2C(O)CH_2CH_2CH_2CH_2CH_2CH_2CH_2CH_2OSO_3Na$,
$CH_3CH_2CH_2C(O)CH_2CH_2CH_2CH_2CH_2CH_2CH_2OSO_3Na$,
$CH_3CH_2CH_2CH_2C(O)CH_2CH_2CH_2CH_2CH_2CH_2OSO_3Na$,
$CH_3CH_2CH_2CH_2CH_2C(O)CH_2CH_2CH_2CH_2CH_2OSO_3Na$,
$CH_3CH_2CH_2CH_2CH_2CH_2C(O)CH_2CH_2CH_2CH_2OSO_3Na$,
$CH_3CH_2CH_2CH_2CH_2CH_2CH_2C(O)CH_2CH_2CH_2OSO_3Na$,
$CH_3CH_2CH_2CH_2CH_2CH_2CH_2CH_2C(O)CH_2CH_2OSO_3Na$,
$CH_3CH_2CH_2CH_2CH_2CH_2CH_2CH_2CH_2C(O)CH_2OSO_3Na$,
$CH_3C(O)CH_2CH_2CH_2CH_2CH_2CH_2CH_2CH_2CH_2OCH_2CH_2OSO_3Na$,
$CH_3C(O)CH_2CH_2CH_2CH_2CH_2CH_2CH_2CH_2C(O)NHCH_2OSO_3Na$,
$CH_3C(O)CH_2CH_2CH_2CH_2CH_2CH_2CH_2CH_2CH_2NHC(O)CH_2OSO_3Na$,
$CH_3C(O)CH_2CH_2CH_2CH_2CH_2CH_2CH_2CH_2CH_2C(O)OSO_3Na$,
$CH_3C(O)CH_2CH_2CH_2CH_2CH_2CH_2CH_2CH_2CH_2C(O)OCH_2OSO_3Na$,
$CH_3C(O)CH_2CH_2CH_2CH_2CH_2CH_2CH_2CH_2CH_2OC(O)CH_2OSO_3Na$,
$CH_3C(O)CH_2CH_2CH_2CH_2CH_2CH_2CH_2CH_2CH_2OSO_3H$,
$CH_3C(O)CH_2CH_2CH_2CH_2CH_2CH_2CH_2CH_2CH_2OSO_3Li$,
$CH_3C(O)CH_2CH_2CH_2CH_2CH_2CH_2CH_2CH_2CH_2OSO_3K$,
$CH_3C(O)CH_2CH_2CH_2CH_2CH_2CH_2CH_2CH_2CH_2OSO_3NH_4$,
$CH_3C(O)CH_2CH_2CH_2CH_2CH_2CH_2CH_2CH_2CH(CH_3)_2OSO_3Na$,
$CH_3C(O)CH_2CH_2CH_2CH_2CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2CH_2OSO_3Na$,
$CH_3C(O)CH_2CH_2CH_2CH_2CH_2CH_2CH_2CH_2CH_2CH_2OSO_3Na$,
$(CH_3)_3CC(O)CH_2CH_2CH_2CH_2CH_2CH_2CH_2CH_2CH_2CH_2CH_2CH_2CH_2CH_2OSO_3Na$,
$(CH_3)_2CHC(O)CH_2CH_2CH_2CH_2CH_2CH_2CH_2CH_2CH_2CH_2CH_2CH_2CH_2CH_2OSO_3Na$,
$(CH_2)_5CHC(O)CH_2CH_2CH_2CH_2CH_2CH_2CH_2CH_2CH_2CH_2CH_2CH_2CH_2CH_2OSO_3Na$,
$CH_3CH_2C(O)CH_2CH_2CH_2CH_2CH_2CH_2CH_2CH_2CH_2CH_2CH_2CH_2CH_2OSO_3Na$,
$CH_3CH_2CH_2CH_2CH_2C(O)CH_2CH_2CH_2CH_2CH_2CH_2CH_2CH_2CH_2OSO_3Na$,
$CH_3CH_2CH_2CH_2CH_2CH_2CH_2C(O)CH_2CH_2CH_2CH_2CH_2CH_2CH_2OSO_3Na$,
$CH_3CH_2CH_2CH_2CH_2CH_2CH_2CH_2CH_2CH_2C(O)CH_2CH_2CH_2CH_2OSO_3Na$,
$CH_3CH_2C(O)CH_2CH_2CH_2CH_2CH_2CH_2CH_2CH_2CH_2CH_2CH_2CH_2OCH_2CH_2OSO_3Na$,
$CH_3CH_2C(O)CH_2CH_2CH_2CH_2CH_2CH_2CH_2CH_2CH_2CH_2CH_2CH_2C(O)NHCH_2OSO_3Na$,
$CH_3CH_2C(O)CH_2CH_2CH_2CH_2CH_2CH_2CH_2CH_2CH_2CH_2CH_2CH_2CH_2NHC(O)CH_2CH_2OSO_3Na$,
$CH_3CH_2C(O)CH_2CH_2CH_2CH_2CH_2CH_2CH_2CH_2CH_2CH_2CH_2CH_2C(O)OCH_2CH_2OSO_3Na$,
$CH_3CH_2C(O)CH_2CH_2CH_2CH_2CH_2CH_2CH_2CH_2CH_2CH_2CH_2CH_2OC(O)CH_2CH_2OSO_3Na$,
$CH_3CH_2C(O)CH_2CH_2CH_2CH_2CH_2CH_2CH_2CH_2CH_2CH_2CH_2C(O)OSO_3Na$,
$CH_3CH_2C(O)CH_2CH_2CH_2CH_2CH_2CH_2CH_2CH_2CH_2CH_2CH_2CH_2CH_2CH_2OSO_3H$,
$CH_3CH_2C(O)CH_2CH_2CH_2CH_2CH_2CH_2CH_2CH_2CH_2CH_2CH_2CH_2CH_2CH_2OSO_3Li$,
$CH_3CH_2C(O)CH_2CH_2CH_2CH_2CH_2CH_2CH_2CH_2CH_2CH_2CH_2CH_2CH_2CH_2OSO_3K$,
$CH_3CH_2C(O)CH_2CH_2CH_2CH_2CH_2CH_2CH_2CH_2CH_2CH_2CH_2CH_2CH_2CH_2OSO_3NH_4$, and
$CH_3C(O)CH_2CH_2CH_2CH_2CH_2CH_2CH_2CH_2CH_2CH_2CH_2CH_2CH_2CH_2CH_2CH_2OSO_3Na$.

The compound of the invention may be produced by a production method including:

a step (11) of hydroxylating a compound (10) represented by the following formula:

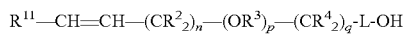

(wherein $R^2$ to $R^4$, L, n, p, and q are defined as described above; and $R^{11}$ is H, a linear or branched alkyl group containing one or more carbon atoms and optionally containing a substituent, or a cyclic alkyl group containing three or more carbon atoms and optionally containing a substituent, and optionally contains a monovalent or divalent heterocycle or optionally forms a ring when containing three or more carbon atoms) to provide a compound (11) represented by the following formula:

[Chem. 6]

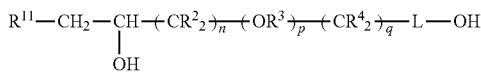

(wherein $R^2$ to $R^4$, $R^{11}$, L, n, p, and q are defined as described above);

a step (12) of oxidizing the compound (11) to provide a compound (12) represented by the following formula:

[Chem. 7]

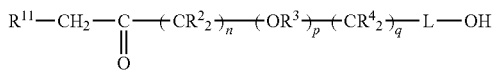

(wherein $R^2$ to $R^4$, $R^{11}$, L, n, p, and q are defined as described above); and a step (13) of sulfuric-esterifying the compound (12) to provide a compound (13) represented by the following formula:

[Chem. 8]

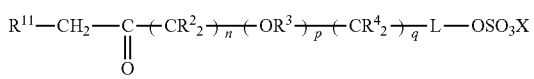

(wherein $R^2$ to $R^4$, $R^{11}$, L, n, p, q, and X are defined as described above).

The alkyl group for $R^{11}$ is preferably free from a carbonyl group.

In the alkyl group for $R^{11}$, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

$R^{11}$ is preferably H, a C1-C9 linear or branched alkyl group optionally containing a substituent, or a C3-C9 cyclic alkyl group optionally containing a substituent, more preferably H, a C1-C9 linear or branched alkyl group free from a carbonyl group, or a C3-C9 cyclic alkyl group free from a carbonyl group, still more preferably H or a C1-C9 linear or branched alkyl group free from a substituent, further more preferably H, a methyl group ($-CH_3$), or an ethyl group ($-C_2H_5$), particularly preferably H or a methyl group ($-CH_3$), most preferably H.

The hydroxylation in the step (11) may be performed by a method (1) in which iron(II) phthalocyanine (Fe(Pc)) and sodium borohydride are allowed to act on the compound (10) in an oxygen atmosphere or a method (2) in which isopinocampheylborane ($IpcBH_2$) is allowed to act on the compound (10) and then the resulting intermediate (dialkyl borane) is oxidized.

In the method (1), iron(II) phthalocyanine may be used in a catalytic amount, and may be used in an amount of 0.001 to 1.2 mol relative to 1 mol of the compound (10).

In the method (1), sodium borohydride may be used in an amount of 0.5 to 20 mol relative to 1 mol of the compound (10).

The reaction in the method (1) may be performed in a solvent. The solvent is preferably an organic solvent, such as an ether, a halogenated hydrocarbon, an aromatic hydrocarbon, a nitrile, or a nitrogen-containing polar organic compound.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

Examples of the nitrogen-containing polar organic compound include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

The reaction temperature in the method (1) is preferably −78° C. to 200° C., more preferably 0° C. to 150° C.

The reaction pressure in the method (1) is preferably 0 to 5.0 MPa, more preferably 0.1 to 1.0 MPa.

The reaction duration in the method (1) is preferably 0.1 to 72 hours, more preferably 0.1 to 48 hours.

In the method (2), isopinocampheylborane may be used in an amount of 1.0 to 10.0 mol relative to 1 mol of the compound (10).

The reaction of the compound (10) and isopinocampheylborane may be performed in a solvent. The solvent is preferably an organic solvent, such as an ether, a halogenated hydrocarbon, or an aromatic hydrocarbon.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The temperature of the reaction of the compound (10) and isopinocampheylborane is preferably −78° C. to 200° C., more preferably 0° C. to 150° C.

The pressure of the reaction of the compound (10) and isopinocampheylborane is preferably 0 to 5.0 MPa, more preferably 0.1 to 1.0 MPa.

The duration of the reaction of the compound (10) and isopinocampheylborane is preferably 0.1 to 72 hours, more preferably 0.1 to 48 hours.

The oxidation in the method (2) may be performed by allowing an oxidizing agent to act on the intermediate. An example of the oxidizing agent is hydrogen peroxide. The oxidizing agent may be used in an amount of 0.7 to 10 mol relative to 1 mol of the intermediate.

The oxidation in the method (2) may be performed in a solvent. Examples of the solvent include water, methanol, and ethanol. Water is preferred.

The oxidation temperature in the method (2) is preferably 0° C. to 100° C., more preferably 0° C. to 80° C.

The oxidation pressure in the method (2) is preferably 0 to 5.0 MPa, more preferably 0.1 to 1.0 MPa.

The oxidation duration in the method (2) is preferably 0.1 to 72 hours, more preferably 0.1 to 48 hours.

The oxidation of the compound (11) in the step (12) may be performed by, for example, (a) a method using the Jones reagent ($CrO_3/H_2SO_4$) (Jones oxidation), (b) a method using Dess-Martin periodinane (DMP) (Dess-Martin oxidation), (c) a method using pyridinium chlorochromate (PCC), (d) a method of allowing a bleaching agent (about 5% to 6% aqueous solution of NaOCl) to act in the presence of a nickel compound such as $NiCl_2$, or (e) a method of allowing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (12) may be performed in a solvent. The solvent is preferably any of water and organic solvents, such as water, ketones, ethers, halogenated hydrocarbons, aromatic hydrocarbons, and nitriles.

Examples of the ketones include acetone, methyl ethyl ketone, methyl isobutyl ketone, cyclohexanone, and diacetone alcohol. Acetone is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

Examples of the nitriles include acetonitrile, propionitrile, butyronitrile, isobutyronitrile, and benzonitrile. Acetonitrile is preferred.

The oxidation temperature in the step (12) is preferably −78° C. to 200° C., and may appropriately be selected in accordance with the method used.

The oxidation pressure in the step (12) is preferably 0 to 5.0 MPa, and may appropriately be selected in accordance with the method used.

The oxidation duration in the step (12) is preferably 0.1 to 72 hours, and may appropriately be selected in accordance with the method used.

The sulfuric-esterification in the step (13) may be performed by reacting the compound (12) and a sulfating reagent. Examples of the sulfating reagent include sulfur trioxide amine complexes such as a sulfur trioxide pyridine complex, a sulfur trioxide trimethylamine complex, and a sulfur trioxide triethylamine complex, sulfur trioxide amide complexes such as a sulfur trioxide dimethylformamide complex, sulfuric acid-dicyclohexylcarbodiimide, chlorosulfuric acid, concentrated sulfuric acid, and sulfamic acid. The amount of the sulfating reagent used is preferably 0.5 to 10 mol, more preferably 0.5 to 5 mol, still more preferably 0.7 to 4 mol, relative to 1 mol of the compound (12).

The sulfuric-esterification in the step (13) may be performed in a solvent. The solvent is preferably an organic solvent, such as an ether, a halogenated hydrocarbon, an aromatic hydrocarbon, pyridine, dimethyl sulfoxide, sulfolane, or a nitrile.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

The sulfuric-esterification temperature in the step (13) is preferably −78° C. to 200° C., more preferably −20° C. to 150° C.

The sulfuric-esterification pressure in the step (13) is preferably 0 to 10 MPa, more preferably 0.1 to 5 MPa.

The sulfuric-esterification duration in the step (13) is preferably 0.1 to 72 hours, more preferably 0.1 to 48 hours.

The compound of the invention may also be produced by a production method including:

a step (21) of ozonolyzing a compound (20) represented by the following formula:

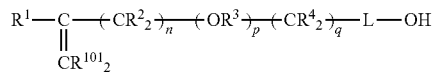

[Chem. 9]

(wherein $R^1$ to $R^4$, L, n, p, and q are defined as described above; and $R^{101}$ is an organic group) to provide a compound (21) represented by the following formula:

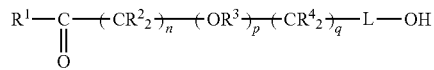

[Chem. 10]

(wherein $R^1$ to $R^4$, L, n, p, and q are defined as described above); and a step (22) of sulfuric-esterifying the compound (21) to provide a compound (22) represented by the following formula:

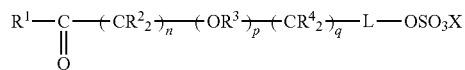

[Chem. 11]

(wherein $R^1$ to $R^4$, L, n, p, q, and X are defined as described above).

$R^{101}$s are each preferably a C1-C20 alkyl group. The two $R^{101}$'s are the same as or different from each other.

The ozonolysis in the step (21) may be performed by allowing ozone to act on the compound (20), followed by post-treatment with a reducing agent.

The ozone may be generated by dielectric barrier discharge in oxygen gas.

Examples of the reducing agent used in the post-treatment include zinc, dimethyl sulfide, thiourea, and phosphines. Phosphines are preferred.

The ozonolysis in the step (21) may be performed in a solvent. The solvent is preferably any of water and organic solvents, such as water, alcohols, carboxylic acids, ethers, halogenated hydrocarbons, and aromatic hydrocarbons.

Examples of the alcohols include methanol, ethanol, 1-propanol, and isopropanol. Methanol and ethanol are preferred.

Examples of the carboxylic acids include acetic acid and propionic acid. Acetic acid is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

The ozonolysis temperature in the step (21) is preferably $-78°$ C. to $200°$ C., more preferably $0°$ C. to $150°$ C.

The ozonolysis pressure in the step (21) is preferably 0 to 5.0 MPa, more preferably 0.1 to 1.0 MPa.

The ozonolysis duration in the step (21) is preferably 0.1 to 72 hours, more preferably 0.1 to 48 hours.

The sulfuric-esterification in the step (22) may be performed by reacting the compound (21) and a sulfating reagent under the same conditions as in the sulfuric-esterification in the step (13).

The compound of the invention may also be produced by a production method including:

a step (31) of epoxidizing a compound (30) represented by the following formula:

$$R^{21}-CH=CH-(CR^2{}_2)_n-(OR^3)_p-(CR^4{}_2)_q-L-OH$$

(wherein $R^2$ to $R^4$, L, n, p, and q are defined as described above; $R^{21}$ is H, a linear or branched alkyl group containing one or more carbon atoms and optionally containing a substituent, or a cyclic alkyl group containing three or more carbon atoms and optionally containing a substituent, and optionally contains a monovalent or divalent heterocycle or optionally forms a ring when containing three or more carbon atoms) to provide a compound (31) represented by the following formula:

[Chem. 12]

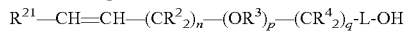

(wherein $R^2$ to $R^4$, $R^{21}$, L, n, p, and q are defined as described above);

a step (32) of reacting the compound (31) with a dialkylcopper lithium represented by $R^{22}{}_2CuLi$ (wherein $R^{22}$ is a linear or branched alkyl group containing one or more carbon atoms and optionally containing a substituent or a cyclic alkyl group containing three or more carbon atoms and optionally containing a substituent, and optionally contains a monovalent or divalent heterocycle or optionally forms a ring when containing three or more carbon atoms) to provide a compound (32) represented by the following formula:

[Chem. 13]

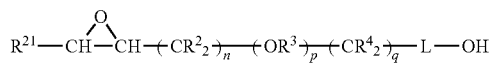

(wherein $R^2$ to $R^4$, $R^{21}$, $R^{22}$, L, n, p, and q are defined as described above);

a step (33) of oxidizing the compound (32) to provide a compound (33) represented by the following formula:

[Chem. 14]

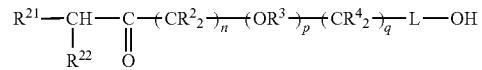

(wherein $R^2$ to $R^4$, $R^{21}$, $R^{22}$, L, n, p, and q are defined as described above); and a step (34) of sulfuric-esterifying the compound (33) to provide a compound (34) represented by the following formula:

[Chem. 15]

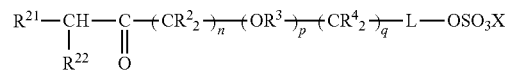

(wherein $R^2$ to $R^4$, $R^{21}$, $R^{22}$, L, n, p, q, and X are defined as described above).

The alkyl group for $R^{21}$ is preferably free from a carbonyl group.

In the alkyl group for $R^{21}$, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

$R^{21}$ is preferably H, a C1-C8 linear or branched alkyl group optionally containing a substituent, or a C3-C8 cyclic alkyl group optionally containing a substituent, more preferably H, a C1-C8 linear or branched alkyl group free from a carbonyl group, or a C3-C8 cyclic alkyl group free from a carbonyl group, still more preferably H or a C1-C8 linear or branched alkyl group free from a substituent, particularly preferably H or a methyl group ($-CH_3$), most preferably H.

The alkyl group for $R^{22}$ is preferably free from a carbonyl group.

In the alkyl group for $R^{22}$, 75% or less of the hydrogen atoms binding to any of the carbon atoms may be replaced by halogen atoms, 50% or less thereof may be replaced by halogen atoms, or 25% or less thereof may be replaced by halogen atoms. The alkyl group is preferably a non-halogenated alkyl group containing no halogen atoms such as fluorine atoms and chlorine atoms.

The alkyl group preferably contains no substituent.

$R^{22}$ is preferably a C1-C9 linear or branched alkyl group optionally containing a substituent or a C3-C9 cyclic alkyl group optionally containing a substituent, more preferably a C1-C9 linear or branched alkyl group free from a carbonyl group or a C3-C9 cyclic alkyl group free from a carbonyl group, still more preferably a C1-C9 linear or branched alkyl group free from a substituent, particularly preferably a methyl group ($-CH_3$) or an ethyl group ($-C_2H_5$), most preferably a methyl group ($-CH_3$).

Two $R^{22}$s are the same as or different from each other.

$R^{21}$ and $R^{22}$ preferably contain 1 to 7 carbon atoms, more preferably 1 or 2 carbon atoms, most preferably 1 carbon atom, in total.

The epoxidation in the step (31) may be performed by allowing an epoxidizing agent to act on the compound (30).

Examples of the epoxidizing agent include peroxy acids such as meta-chloroperbenzoic acid (m-CPBA), perbenzoic acid, hydrogen peroxide, and tert-butyl hydroperoxide, dimethyl dioxolane, and methyl trifluoromethyl dioxolane. Peroxy acids are preferred, and meta-chloroperbenzoic acid is more preferred.

The epoxidizing agent may be used in an amount of 0.5 to 10.0 mol relative to 1 mol of the compound (30).

The epoxidation in the step (31) may be performed in a solvent. The solvent is preferably an organic solvent, such as a ketone, an ether, a halogenated hydrocarbon, an aromatic hydrocarbon, a nitrile, pyridine, a nitrogen-containing polar organic compound, or dimethyl sulfoxide. Dichloromethane is preferred.

Examples of the ketone include acetone, methyl ethyl ketone, methyl isobutyl ketone, cyclohexanone, and diacetone alcohol. Acetone is preferred.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

Examples of the nitrile include acetonitrile, propionitrile, butyronitrile, isobutyronitrile, and benzonitrile. Acetonitrile is preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

The epoxidation temperature in the step (31) is preferably −78° C. to 200° C., more preferably −40° C. to 150° C.

The epoxidation pressure in the step (31) is preferably 0 to 5.0 MPa, more preferably 0.1 to 1.0 MPa.

The epoxidation duration in the step (31) is preferably 0.1 to 72 hours, more preferably 0.1 to 48 hours.

In the step (32), the dialkylcopper lithium may be used in an amount of 0.5 to 1.0.0 mol relative to 1 mol of the compound (31).

The reaction in the step (32) may be performed in a solvent. The solvent is preferably an organic solvent, such as an ether, a halogenated hydrocarbon, or an aromatic hydrocarbon.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The reaction temperature in the step (32) is preferably −78° C. to 200° C., more preferably −40° C. to 150° C.

The reaction pressure in the step (32) is preferably 0 to 5.0 MPa, more preferably 0.1 to 1.0 MPa.

The reaction duration in the step (32) is preferably 0.1 to 72 hours, more preferably 0.1 to 48 hours.

The oxidation of the compound (32) in the step (33) may be performed by, for example, (a) a method of using the Jones reagent ($CrO_3/H_2SO_4$) (Jones oxidation), (b) a method of using Dess-Martin periodinane (DMP) (Dess-Martin oxidation), (c) a method of using pyridinium chlorochromate (PCC), (d) a method of allowing a bleaching agent (about 5% to 6% aqueous solution of NaOCl) to act in the presence of a nickel compound such as $NiCl_2$, or (e) a method of allowing a hydrogen acceptor such as an aldehyde or a ketone to act in the presence of an aluminum catalyst such as $Al(CH_3)_3$ or $Al[OCH(CH_3)_2]_3$ (Oppenauer oxidation).

The oxidation in the step (33) may be performed in a solvent. The solvent is preferably any of water and organic solvents, such as water, ketones, alcohols, ethers, halogenated hydrocarbons, aromatic hydrocarbons, and nitriles.

Examples of the ketones include acetone, methyl ethyl ketone, methyl isobutyl ketone, cyclohexanone, and diacetone alcohol. Acetone is preferred.

Examples of the alcohols include methanol, ethanol, 1-propanol, and isopropanol. Methanol and ethanol are preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the aromatic hydrocarbons include benzene, toluene, and xylene. Benzene and toluene are preferred.

Examples of the nitriles include acetonitrile, propionitrile, butyronitrile, isobutyronitrile, and benzonitrile. Acetonitrile is preferred.

The oxidation temperature in the step (33) is preferably −78° C. to 200° C., and may appropriately be selected in accordance with the method used.

The oxidation pressure in the step (33) is preferably 0 to 5.0 MPa, and may appropriately be selected in accordance with the method used.

The oxidation duration in the step (33) is preferably 0.1 to 72 hours, and may appropriately be selected in accordance with the method used.

The sulfuric-esterification in the step (34) may be performed by reacting the compound (33) and a sulfating reagent under the same conditions as in the sulfuric-esterification in the step (13).

The compound of the invention may also be produced by a production method including:

a step (41) of oxidizing a compound (10) represented by the following formula:

$$R^{11}-CH=CH-(CR^2_2)_n-(OR^3)_p-(CR^4_2)_q-L-OH$$

(wherein $R^2$ to $R^4$, $R^{11}$, L, n, p, and q are defined as described above) to provide a compound (41) represented by the following formula:

[Chem. 16]

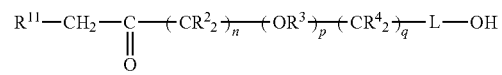

(wherein $R^2$ to $R^4$, $R^{11}$, L, n, p, and q are defined as described above); and a step (42) of sulfuric-esterifying the compound (41) to provide a compound (42) represented by the following formula:

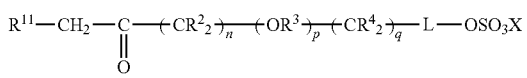

(wherein $R^2$ to $R^4$, $R^{11}$, L, n, p, q, and X are defined as described above).

L is preferably a single bond.

The oxidation in the step (41) may be performed by allowing an oxidizing agent to act on the compound (10) in the presence of water and a palladium compound.

Examples of the oxidizing agent include monovalent or divalent copper salts such as copper chloride, copper acetate, copper cyanide, and copper trifluoromethanethiolate, iron salts such as iron chloride, iron acetate, iron cyanide, iron trifluoromethanethiolate, and hexacyanoferrates, benzoquinones such as 1,4-benzoquinone, 2,3-dichloro-5,6-dicyano-1,4-benzoquinone, tetrachloro-1,2-benzoquinone, and tetrachloro-1,4-benzoquinone, $H_2O_2$, $MnO_2$, $KMnO_4$, $RuO_4$, m-chloroperbenzoic acid, peracetic acid, perbenzoic acid, tert-butyl hydroperoxide, cumene hydroperoxide, potassium persulfate, mixtures of potassium hydrogen persulfate-potassium hydrogen sulfate-potassium sulfate, and oxygen. Copper salts, iron salts, benzoquinones, mixtures of potassium hydrogen persulfate-potassium hydrogen sulfate-potassium sulfate, and oxygen-based compounds are preferred, and copper chloride, iron chloride, 1,4-benzoquinone, and oxygen are more preferred.

The oxidizing agent may be used in an amount of 0.001 to 10 mol relative to 1 mol of the compound (10).

The water may be used in an amount of 0.5 to 1000 mol relative to 1 mol of the compound (10).

An example of the palladium compound is palladium dichloride. The palladium compound may be used in a catalytic amount, and may be used in an amount of 0.0001 to 1.0 mol relative to 1 mol of the compound (10).

The oxidation in the step (41) may be performed in a solvent. Examples of the solvent include water, esters, aliphatic hydrocarbons, aromatic hydrocarbons, alcohols, carboxylic acids, ethers, halogenated hydrocarbons, nitrogen-containing polar organic compounds, nitriles, dimethyl sulfoxide, and sulfolane.

Examples of the esters include ethyl acetate, butyl acetate, ethylene glycol monomethyl ether acetate, and propylene glycol monomethyl ether acetate (PGMEA, also known as 1-methoxy-2-acetoxypropane). Ethyl acetate is preferred.

Examples of the aliphatic hydrocarbons include hexane, cyclohexane, heptane, octane, nonane, decane, undecane, dodecane, and mineral spirits. Cyclohexane and heptane are preferred.

Examples of the aromatic hydrocarbons include benzene, toluene, and xylene. Benzene and toluene are preferred.

Examples of the alcohols include methanol, ethanol, 1-propanol, and isopropanol.

Examples of the carboxylic acids include acetic acid and propionic acid. Acetic acid is preferred.

Examples of the ethers include diethyl ether, tetrahydrofuran, dioxane, and diethylene glycol diethyl ether. Diethyl ether and tetrahydrofuran are preferred.

Examples of the halogenated hydrocarbons include dichloromethane, dichloroethane, chloroform, chlorobenzene, and o-dichlorobenzene. Dichloromethane and chloroform are preferred.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the nitriles include acetonitrile, propionitrile, butyronitrile, isobutyronitrile, and benzonitrile. Acetonitrile is preferred.

The oxidation temperature in the step (41) is preferably −78° C. to 200° C., more preferably −20° C. to 150° C.

The oxidation pressure in the step (41) is preferably 0 to 10 MPa, more preferably 0.1 to 5.0 MPa.

The oxidation duration in the step (41) is preferably 0.1 to 72 hours, more preferably 0.1 to 48 hours.

The sulfuric-esterification in the step (42) may be performed by reacting the compound (41) and a sulfating reagent under the same conditions as in the sulfuric-esterification in the step (13).

The compound of the invention may also be produced by a production method including:

a step (51) of reacting a compound (50) represented by the following formula:

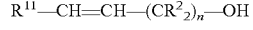

(wherein $R^2$, $R^{11}$, and n are defined as described above) with a halogenating agent to provide a compound (51) represented by the following formula:

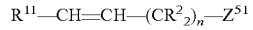

(wherein $R^2$, $R^{11}$, and n are defined as described above; and $Z^{51}$ is a halogen atom);

a step (52) of reacting the compound (51) with an alkylene glycol represented by HO—$R^3$-L-OH (where L and $R^3$ are defined as described above) to provide a compound (52) represented by the following formula:

(wherein $R^2$, $R^3$, $R^{11}$, L, and n are defined as described above);

a step (53) of oxidizing the compound (52) to provide a compound (53) represented by the following formula:

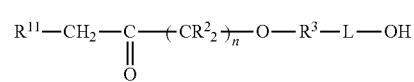

(wherein $R^2$, $R^3$, $R^{11}$, L, and n are defined as described above); and a step (54) of sulfuric-esterifying the compound (53) to provide a compound (54) represented by the following formula:

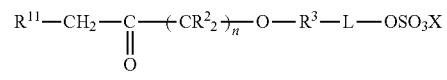

(wherein $R^2$, $R^3$, $R^{11}$, L, n, and X are defined as described above).

$Z^{51}$ is preferably F, Cl, Br, or I, more preferably Br.

Examples of the halogenating agent used in the step (51) include N-bromosuccinimide and N-chlorosuccinimide.

The halogenating agent may be used in an amount of 0.5 to 10.0 mol per 1 mol of the compound (50).

The reaction in the step (51) may be performed in the presence of a phosphine such as triphenyl phosphine.

The phosphine may be used in an amount of 0.5 to 10.0 mol per 1 mol of the compound (50).

The reaction in the step (51) may be performed in a solvent. The solvent is preferably an organic solvent, such as an ether, a halogenated hydrocarbon, or an aromatic hydrocarbon.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The reaction temperature in the step (51) is preferably −78° C. to 200° C., more preferably −40° C. to 150° C.

The reaction pressure in the step (51) is preferably 0 to 5.0 MPa, more preferably 0.1 to 1.0 MPa.

The reaction duration in the step (51) is preferably 0.1 to 72 hours, more preferably 0.1 to 48 hours.

In the step (52), the alkylene glycol may be used in an amount of 0.5 to 10.0 mol per 1 mol of the compound (51).

The reaction in the step (52) may be performed in the presence of a base. Examples of the base include sodium hydride, sodium hydroxide, and potassium hydroxide.

The base may be used in an amount of 0.5 to 10.0 mol per 1 mol of the compound (51).

The reaction in the step (52) may be performed in a solvent. The solvent is preferably an organic solvent, such as a nitrogen-containing polar organic compound, an ether, a halogenated hydrocarbon, or an aromatic hydrocarbon.

Examples of the nitrogen-containing polar organic compounds include N,N-dimethylformamide, N,N-dimethylacetamide, N-methyl-2-pyrrolidone, 2-pyrrolidone, and 1,3-dimethyl-2-imidazolidinone. N,N-dimethylformamide, N,N-dimethylacetamide, and N-methyl-2-pyrrolidone are preferred.

Examples of the ether include diethyl ether, tetrahydrofuran, dioxane, and diethylene glycol diethyl ether. Diethyl ether and tetrahydrofuran are preferred.

Examples of the halogenated hydrocarbon include dichloromethane, dichloroethane, chloroform, chlorobenzene, and o-dichlorobenzene. Dichloromethane and chloroform are preferred.

Examples of the aromatic hydrocarbon include benzene, toluene, and xylene. Benzene and toluene are preferred.

The reaction temperature in the step (52) is preferably −78° C. to 200° C., more preferably −40° C. to 150° C.

The reaction pressure in the step (52) is preferably 0 to 5.0 MPa, more preferably 0.1 to 1.0 MPa.

The reaction duration in the step (52) is preferably 0.1 to 72 hours, more preferably 0.1 to 48 hours.

The oxidation in the step (53) may be performed by allowing an oxidizing agent to act on the compound (52) in the presence of water and a palladium compound under the same conditions as in the oxidation in the step (41).

The sulfuric-esterification in the step (54) may be performed by reacting the compound (53) and a sulfating reagent under the same conditions as in the sulfuric-esterification in the step (13).

In any of the production methods described above, the resulting compounds may be subjected to any of evaporation of a solvent or operations such as distillation and purification after the respective steps, whereby the purity of each compound may be increased. When the resulting compound contains a group represented by —$OSO_3H$ (i.e., when X is H), the compound may be brought into contact with an alkali such as sodium carbonate or ammonia so that —$OSO_3H$ may be converted into a sulfuric acid salt group.

Preferred among the above production methods is a production method including the steps (41) and (42). The production method including the steps (41) and (42) is also one aspect of the invention.

EXAMPLES

The invention is described with reference to examples, but the invention is not intended to be limited by these examples.

The parameters in the examples were determined by the following method.

$^1$H-NMR Measurement

The $^1$H-NMR measurement was performed using a nuclear magnetic resonance device, NMR system 400 available from VARIAN Inc. Tetramethylsilane was added as an internal standard to the sample, and the value of tetramethylsilane was set to 0 ppm in the measurement.

Example 1

A mixture of 10-undecen-1-ol (16 g), 1,4-benzoquinone (10.2 g), DMF (160 mL), water (16 mL), and $PdCl_2$ (0.34 g) was heated and stirred at 90° C. for 12 hours.

The solvent was then evaporated under reduced pressure. The resulting residue was subjected to liquid separation and purified by column chromatography, whereby 11-hydroxyundecan-2-one (15.4 g) was obtained.

The spectrum data of the resulting 11-hydroxyundecan-2-one are the following.

$^1$H-NMR ($CDCl_3$) δ ppm: 1.29-1.49 (m, 14H), 2.08 (s, 3H), 2.45 (J=7.6, t, 2H), 3.51 (J=6.5, t, 2H)

A mixture of 11-hydroxyundecan-2-one (13 g), a sulfur trioxide triethylamine complex (13.9 g), and tetrahydrofuran (140 mL) was stirred at 50° C. for 12 hours. A solution of sodium methoxide (3.8 g) in methanol (12 mL) was dropwise added to the reaction solution.

The solid precipitate was filtered under reduced pressure and the residue was washed with ethyl acetate, whereby sodium 10-oxounedecyl sulfate (15.5 g) was obtained. The spectrum data of the resulting sodium 10-oxounedecyl sulfate are the following.

$^1$H-NMR ($CDCl_3$) δ ppm: 1.08 (J=6.8, m, 10H), 1.32 (m, 2H), 1.45 (m, 2H), 1.98 (s, 3H), 2.33 (J=7.6, t, 2H), 3.83 (J=6.5, t, 2H)

Example 2

Sodium 22-oxotricosyl sulfate was synthesized in the same manner as in Example 1, except that the material was changed from 10-undecen-1-ol to 22-tricosen-1-ol.

Example 3

A mixture of 10-undecen-1-ol (35 g), triphenylphosphine (59 g), dichloromethane (350 mL), and N-bromosuccinimide (40 g) was heated and stirred at 0° C. for 24 hours.

The solvent was then evaporated under reduced pressure. The resulting residue was mixed with heptane and extracted, and the solvent was evaporated under reduced pressure. The residue was purified by column chromatography, whereby 11-bromo-1-undecene (45 g) was obtained.

The spectrum data of the resulting 11-bromo-1-undecene are the following.

$^1$H-NMR (CDCl$_3$) δ ppm: 1.29-1.39 (m, 12H), 1.80-1.90 (m, 2H), 2.00-2.08 (m, 2H), 3.38-3.43 (t, J=6.8, 2H), 4.91-5.03 (m, 2H), 5.74-5.89 (m, 1H)

A mixture of 11-bromo-1-undecene (21 g), NaH (4.3 g), ethylene glycol (11 g), and DMF (100 mL) was stirred at 80° C. for 4 hours. The reaction solution was mixed with a saturated ammonium chloride solution (300 mL), and the mixture was extracted with ethyl acetate. The extract was dried over sodium sulfate, and the solvent was evaporated under reduced pressure. The residue was purified by silica gel column chromatography, whereby 2-(10-undecenyl-1-oxy)ethanol (11 g) was obtained.

The spectrum data of the resulting 2-(10-undecenyl-1-oxy)ethanol are the following.

$^1$H-NMR (CDCl$_3$) δ ppm: 1.28-1.34 (m, 12H), 1.50-1.61 (m, 2H), 1.94-2.12 (m, 2H), 3.44-3.55 (m, 4H), 3.70-3.75 (m, 2H), 4.91-5.02 (m, 2H), 5.73-5.88 (m, 1H)

A mixture of 2-(10-undecenyl-1-oxy)ethanol (3.0 g), 1,4-benzoquinone (1.5 g), DMF (30 mL), water (3 mL), and PdCl$_2$ (0.050 g) was heated and stirred at 90° C. for 24 hours.

The solvent was then evaporated under reduced pressure. The resulting residue was purified by liquid separation, column chromatography, and recrystallization, whereby 11-(2-hydroxyethoxy)undecan-2-one (2.1 g) was obtained.

The spectrum data of the resulting 11-(2-hydroxyethoxy) undecan-2-one are the following.

$^1$H-NMR (CDCl$_3$) δ ppm: 1.27-1.42 (m, 10H), 1.43-1.57 (m, 4H), 2.12 (s, 3H), 2.38-2.43 (t, J=7.6, 2H), 3.45-3.55 (m, 4H), 3.69-3.74 (m, 2H)

A mixture of 11-(2-hydroxyethoxy)undecan-2-one (1.4 g), a sulfur trioxide triethylamine complex (1.3 g), and tetrahydrofuran (15 mL) was stirred at 50° C. for 3 hours. A sodium methoxide (0.34 g)/methanol (1 mL) solution was dropwise added to the reaction solution.

The solid precipitate was filtered under reduced pressure and the residue was washed with ethyl acetate, whereby sodium 2-((10-oxoundecyl)oxy)ethyl sulfate (0.92 g) was obtained. The spectrum data of the resulting sodium 2-((10-oxoundecyl)oxy)ethyl sulfate are the following.

$^1$H-NMR (D$_2$O) δ ppm: 1.03-1.20 (m, 10H), 1.21-1.45 (m, 4H), 1.98 (s, 3H), 2.31-2.36 (t, J=7.3, 2H), 3.34-3.39 (t, J=6.8, 2H), 3.52-3.55 (t, J=4.6, 2H), 3.94-3.97 (t, J=4.6, 2H)

Example 4

Sodium 18-oxononadecyl sulfate was synthesized in the same manner as in Example 1, except that the material was changed from 10-undecen-1-ol to 18-nonadecen-1-ol.

Sodium 10-oxoundecyl sulfate obtained in Example 1 was dissolved in water so as to have a concentration as shown in Table 1, and the surface tension was measured. The surface tension was measured by the Wilhelmy method at 20° C. The results are shown in Table 1.

TABLE 1

|  |  | Amount of compound relative to water (wt %) | | |
|---|---|---|---|---|
|  |  | 0.01 | 0.1 | 1.0 |
| Surface tension (mN/m) | Example 1 | 72.1 | 63.5 | 45.6 |

INDUSTRIAL APPLICABILITY

The compound of the invention can suitably reduce the surface tension of water.

The compound of the invention can suitably be used as a surfactant.

The compound of the invention can suitably be used as a surfactant accelerator (particularly as a surfactant accelerator in coating material, lacquer, adhesive, or the like).

The compound of the invention can suitably be used as a viscosity reducer, for example.

The compound of the invention can suitably be used as a dispersant, particularly an aqueous dispersant, for example.

The compound of the invention can suitably be used as an emulsifier, for example.

The invention claimed is:

1. A compound represented by the following formula:

[Chem. 1]

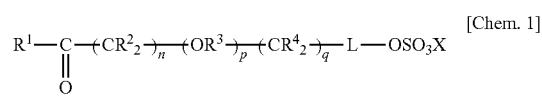

wherein

R$^1$ is a methyl group;

R$^2$ is H and R$^4$ is H or a substituent;

R$^3$ is a C1-C10 alkylene group optionally containing a substituent;

n is an integer of 1 or greater;

p and q are each individually an integer of 0 or greater;

X is H, a metal atom, NR$^5$$_4$, imidazolium optionally containing a substituent, pyridinium optionally containing a substituent, or phosphonium optionally containing a substituent, where R$^5$s are each H or an organic group and are the same as or different from each other;

L is a single bond, —CO$_2$—B—*, —OCO—B—*, —CONR$_6$—B—*, —NR$_6$CO—B—*, or —CO—, where B is a single bond or a C1-C10 alkylene group optionally containing a substituent, R$^6$ is H or a C1-C4 alkyl group optionally containing a substituent, and * indicates the bond to —OSO$_3$X in the formula;

a total number of carbon atoms in the compound is 5 to 30; and the compound excludes 11-keto dodecyl sulphate.

2. The compound according to claim 1, wherein L is a single bond.

3. The compound according to claim 1, wherein R$^4$ is H or a C1-C4 linear or branched alkyl group.

4. The compound according to claim 1, wherein R$^3$ is a C1-C4 alkylene group free from a substituent.

5. The compound according to claim 1, wherein X in the formula is a metal atom or NR$^5$$_4$.

6. The compound according to claim 1, wherein the compound is an aqueous dispersant.

7. A production method for producing the compound of claim 1, the method comprising:

a step of oxidizing a compound represented by the following formula (10):

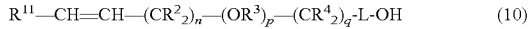   (10)

wherein

R$^2$ is H and R$^4$ is H or a substituent;

R$^3$ is a C1-C10 alkylene group optionally containing a substituent;

n is an integer of 1 or greater;

p and q are each individually an integer of 0 or greater;

R$^{11}$ is H; and

L is a single bond, —CO$_2$—B—*, —OCO—B—*, —CONR$^6$—B—*, —NR$^6$CO—B—*, or —CO—, where B is a single bond or a C1-C10 alkylene group optionally containing a substituent, R$^6$ is H or a C1-C4 alkyl group optionally containing a substituent, and * indicates the bond to —OH in the formula (10), to provide a compound represented by the following formula (41):

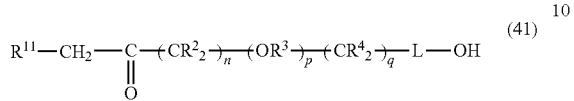
(41)

wherein R$^2$ to R$^4$, R$^{11}$, L, n, p, and q are defined as described above in formula (10); and a step of sulfuric-esterifying the compound represented by formula (41) to provide a compound represented by the following formula (42):

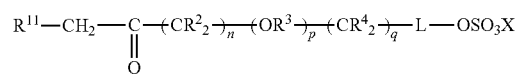
(42)

wherein X is H, a metal atom, NR$^5_4$, imidazolium optionally containing a substituent, pyridinium optionally containing a substituent, or phosphonium optionally containing a substituent, where R$^5$s are each H or an organic group and are the same as or different from each other; and wherein R$^2$ to R$^4$, R$^{11}$, L, n, p, and q are defined as described above in formula (10).

8. The production method according to claim 7, wherein L is a single bond.

\* \* \* \* \*